US008218879B2

(12) United States Patent
Yu et al.

(10) Patent No.: US 8,218,879 B2
(45) Date of Patent: Jul. 10, 2012

(54) SYSTEM AND METHOD FOR SHUTTER DETECTION

(75) Inventors: Songyang Yu, Mississauga (CA); Vittorio Accomazzi, Toronto (CA); Paul Geiger, Toronto (CA)

(73) Assignee: Merge Healthcare Incorporated, Hartland, WI (US)

( * ) Notice: Subject to any disclaimer, the term of this patent is extended or adjusted under 35 U.S.C. 154(b) by 1187 days.

(21) Appl. No.: 11/857,546

(22) Filed: Sep. 19, 2007

(65) Prior Publication Data

US 2008/0069470 A1 Mar. 20, 2008

Related U.S. Application Data

(60) Provisional application No. 60/826,094, filed on Sep. 19, 2006.

(51) Int. Cl.
*G06K 9/48* (2006.01)
(52) U.S. Cl. ......... 382/199; 396/452; 396/471; 352/204
(58) Field of Classification Search .................. 382/254, 382/199; 396/355, 357, 552–504; 352/204–220
See application file for complete search history.

(56) References Cited

U.S. PATENT DOCUMENTS

| | | | |
|---|---|---|---|
| 5,506,913 A | 4/1996 | Ibison et al. | |
| 5,901,240 A | 5/1999 | Luo et al. | |
| 5,978,443 A | 11/1999 | Patel | |
| 5,982,916 A | 11/1999 | Kuhn | |
| 6,459,094 B1 | 10/2002 | Wang et al. | |
| 6,650,725 B2 | 11/2003 | Lutz | |
| 6,775,399 B1 | 8/2004 | Jiang | |
| 2005/0094860 A1 | 5/2005 | Shinbata | |

FOREIGN PATENT DOCUMENTS

| | | |
|---|---|---|
| EP | 0610605 | 8/1994 |
| EP | 0635804 | 1/1995 |
| EP | 0742536 | 11/1996 |
| JP | 6251127 | 9/1994 |

OTHER PUBLICATIONS

Richard Lepage et al, Multiresolution Edge Detection, IEEE 1992.*
First Office Action from Japanese Patent Office for Application No. 2009-528561 dated Sep. 27, 2011 (4 pages).

(Continued)

*Primary Examiner* — Wesley Tucker
*Assistant Examiner* — Mark Roz
(74) *Attorney, Agent, or Firm* — Michael Best & Friedrich LLP

(57) ABSTRACT

A method for removing shutter areas in an image, in particular an x-ray image is provided. Edges are examined in a multi-resolution image pyramid and evaluated to determine potential shutter blade candidates defining the shutter areas. Heuristic rules and/or an automatic classifier such as a Neuronal Network, are applied to distinguish true shutter blades from false positives. The rule set and the classifier are based on a set of features extracted from the potential shutter blade candidates as well as predetermined knowledge of the expected placement of the shutter, human anatomy. Up to four shutter blades are expected to be detected and based on these blades, the bright areas in the image that occur due to the shutters are removed.

15 Claims, 12 Drawing Sheets

(a)

(b)

(c)

(d)

OTHER PUBLICATIONS

International Search Report from PCT/CA2007/001636 completed Nov. 20, 2007 and received by the applicant Jan. 30, 2008.
Gonzalez, R.C. and Woods, Richard E.; Digital image Processing, $2^{nd}$ ed.; pp. 132 to 137; Prentice Hall, 2002.
Canny, J.; "A Computational Approach to Edge Detection"; IEEE Transactions on Pattern Analysis and Machine Intelligence; Nov. 1986; vol. 8, No. 6.
EP Extended Search Report Dated Nov. 19, 2010 for EP07815830.0 9 pgs.

* cited by examiner (a)

(b)

(c)

(d)

(a)

(b)

(c)

(d)

(a)

(b)

(c)

(d)

SYSTEM AND METHOD FOR SHUTTER DETECTION

This application claims priority from U.S. Patent Application No. 60/826,094 filed on Sep. 19, 2006, the contents of which are incorporated herein by reference.

FIELD OF THE INVENTION

The present invention relates generally to image processing and has particular utility in detecting and removing unwanted information such as shutter edges in a medical image.

DESCRIPTION OF THE PRIOR ART

In medical x-ray examinations, opaque materials often referred to as "shutters" are typically used to shield body pails from unnecessary radiation exposure. The shutters are intended to be placed between the radiation beam source and the patient being examined.

Due to the high attenuation of the material used for the shutter, e.g. lead, stainless steel, aluminium etc., the areas in the image that are effectively blocked by the shutters generally appear as bright regions and do not contain any diagnostically useful information but rather are meant to shield an area of the body that is not intended to be imaged. The presence of the bright regions may, in some instances, cause a distraction to a radiologist, e.g. due to glare, and may impair their diagnosis. An x-ray image is digitised as a two-dimensional array of numbers, the magnitudes of which correspond to the intensity of x-rays arriving at the detector. The values may be rescaled in order to maximize the visual contrast in an area of interest. The rescaling a depends in part on the intensity histogram of the x-ray image.

The shadow cast by the shutter does not contain any useful information and would otherwise dominate the intensity histogram by providing a peak. Since these areas in the image defined by the shutters are of no use to a radiologist, it is often desirable to have those shutter areas detected and removed automatically.

It is therefore an object of the following to obviate or mitigate the above disadvantages.

SUMMARY OF THE INVENTION

The following provides a method, apparatus and computer readable medium for detecting and removing unwanted information in a medical image.

In one aspect, there is provided, a method for detecting and removing unwanted information in a medical image comprising: processing the image to obtain edge information; generating a list of at least one candidate edge in the image from the edge information according to predetermined criteria; evaluating each of the at least one candidate edge according to a predetermined rule set to select one or more of the at least one candidate edge that is considered to define the extent of the unwanted information within the image, the evaluating comprising comparing the at least one candidate edge to other information in the image; and removing the unwanted information based on the location of the one or more of the at least one candidate edge in the image.

In another aspect, a computer readable medium is provided carrying instructions for performing the above method.

In yet another aspect, there is provided a system for detecting and removing unwanted information in a medical image comprising: an interface comprising a display for viewing the image and enabling a user to interact with the system; and an image processing program capable of obtaining and processing the image from medical imaging device and displaying the image on the display, the image processing program being configured for processing the image to obtain edge information; generating a list of at least one candidate edge in the image from the edge information according to predetermined criteria; evaluating each of the at least one candidate edge according to a predetermined rule set to select one or more of the at least one candidate edge that is considered to define the extent of the unwanted information within the image, the evaluating comprising comparing the at least one candidate edge to other information in the image; and removing the unwanted information based on the location of the one or more of the at least one candidate edge in the image.

In yet another aspect, there is provided a method for processing a medical image to enable detection and removal of unwanted information in the image, the method comprising obtaining the image, down sampling the image to generate a plurality of image levels having successively decreasing image resolutions, and processing each the image level to obtain edge information to enable edges in the image levels to be evaluated in a lowest level having a lowest resolution and selected edges promoted through successive image levels until a highest of the image levels, wherein selected edges define the extent of the unwanted information.

In yet another aspect, there is provided a method for processing a medical image to enable removal of unwanted information in the image generated during acquisition of the medical image, the method comprising obtaining a pre-processed image having had a gradient operator applied thereto, and applying a Canny edge mask to the pre-processed image to obtain edge information from the medical image for evaluating edge segments to determine the edges defining the extent of the unwanted information.

BRIEF DESCRIPTION OF THE DRAWINGS

An embodiment of the invention will now be described by way of example only with reference to the appended drawings wherein.

DETAILED DESCRIPTION OF THE INVENTION

Figure 1:
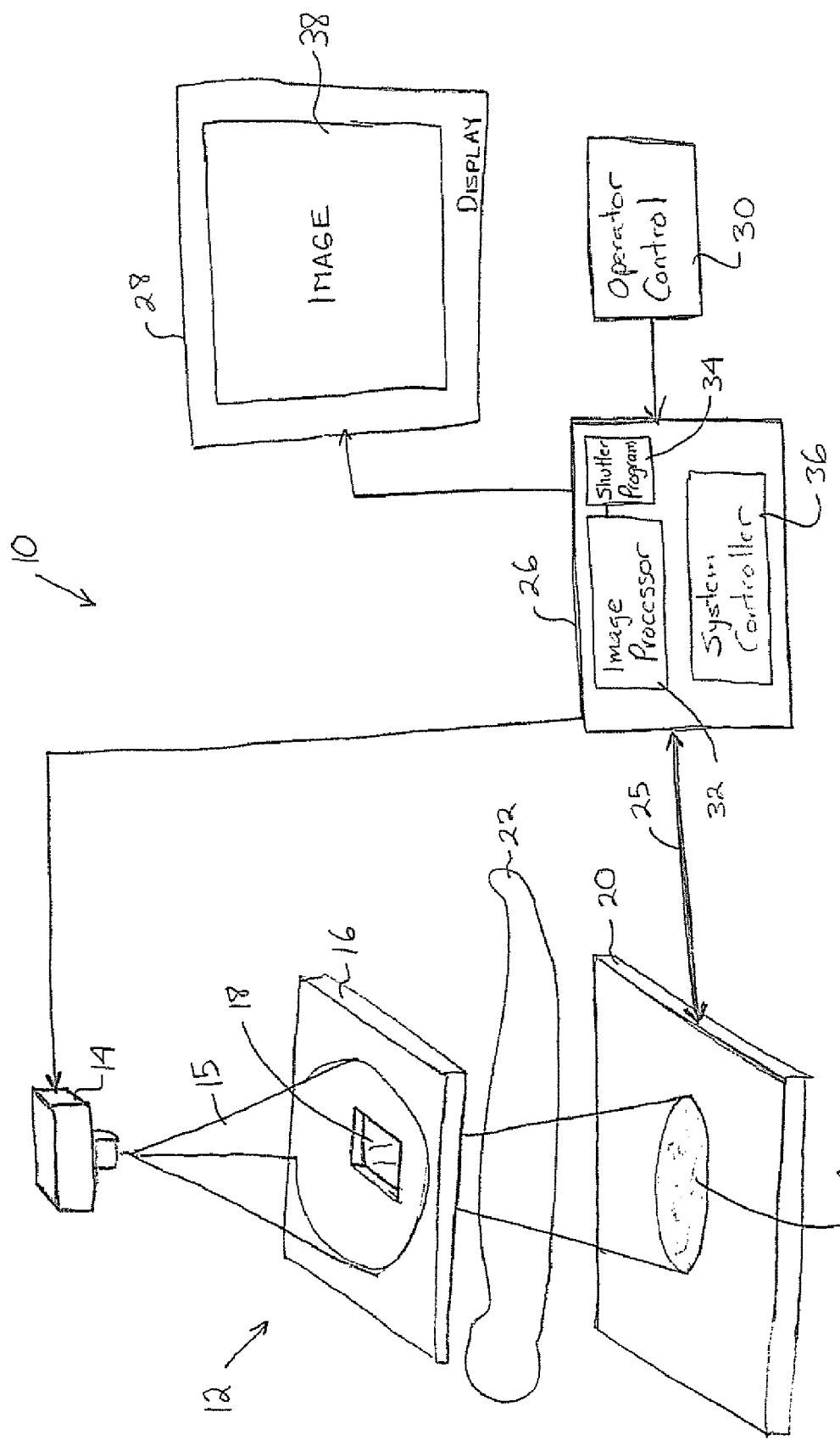
FIG. 1 is a schematic diagram of an x-ray system having a shutter processing program.

Referring to FIG. 1, an x-ray system is generally denoted by numeral 10. The x-ray system 10 comprises an x-ray apparatus 12 having an x-ray source 14, which, when excited by a power supply (not shown), emits an x-ray beam 15. As illustrated, the x-ray beam 15 is directed towards a patient 22 and passes through a shutter 16 disposed between the patient 22 and the source 14.

In the example shown in FIG. 1, the shutter 16 includes an aperture 18 for limiting the amount of beam 15 that passes through the patient 22. The x-rays of the beam 15 that pass through the patient 22 impinge on a photographic detection plate 20 in area 24, which captures an x-ray image of a portion of the patient 22. It will be appreciated that the shutter 16 shown in FIG. 1 is for illustrative purposes only and that the following principles apply to any other arrangement used for obtaining a shuttered image, e.g., a lead apron.

The x-ray system 10 also comprises an x-ray machine 26, which powers the x-ray source 14, acquires the x-rays impinging the detection plate 20, displays a two dimensional image 38 on a display 28 and is operated by a technician using an operator control 30. The machine 26 comprises an image processing program 32 that is responsible for digitizing, and processing the acquired x-ray area 24 according to standard image processing techniques to generate the image 28, a shutter program 34 for automatically detecting and removing shutters from the image 38, and a system controller 36, which is responsible for operating the machine according to technician input at the operator controls 30.

Figure 2:
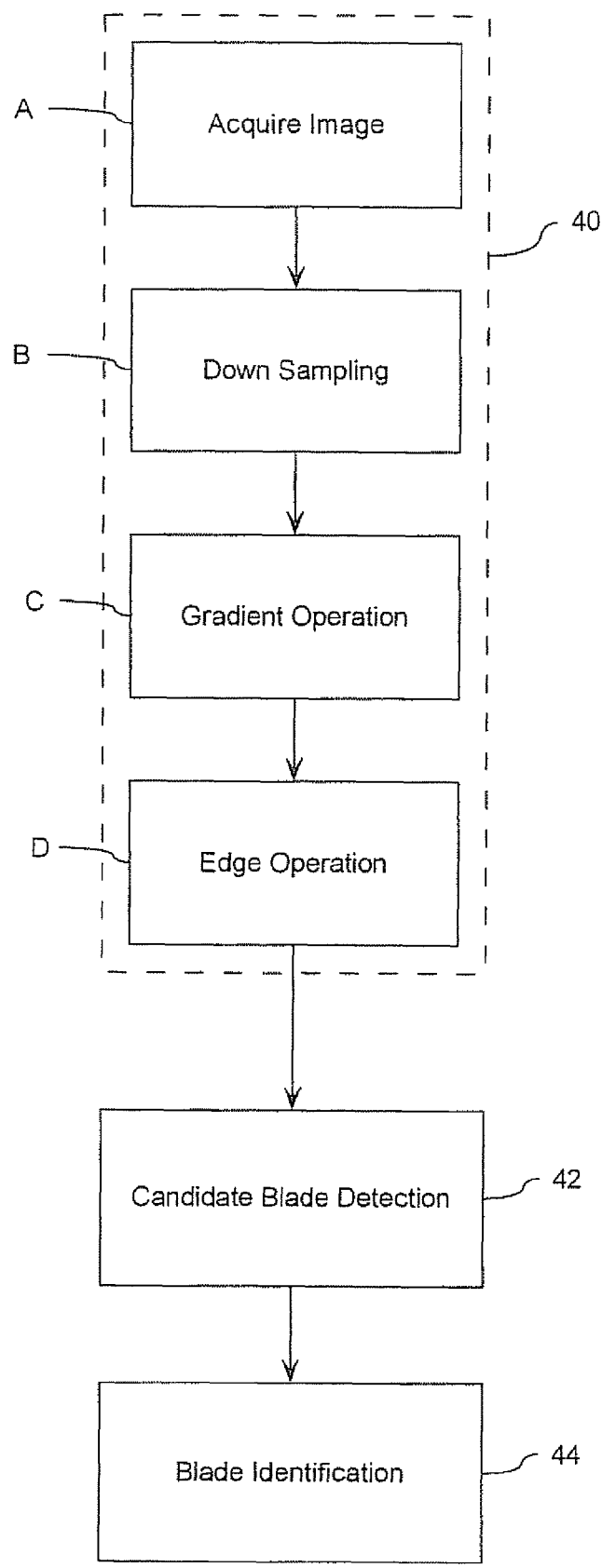
FIG. 2 is a flow chart illustrating the steps performed in a shutter detection procedure.

Referring to FIG. 2, the general stages performed by the x-ray machine 26 under the control of the system controller 36 are shown. The primary stages are a pre-processing stage 40 performed by the image processing program 32 that generates the image data used in a blade detection stage 42 and a blade identification stage 44 performed by the shutter program 34. The pre-processing stage 40 generally comprises acquiring an image using the x-ray apparatus 12 at step A, down sampling the image at step B to create a multiple resolution image pyramid, performing a gradient operation at step C for generating the gradient for each image in the pyramid generated in step B, and performing an edge operation at step D for generating the edge masks for each image in the pyramid.

Figure 3:
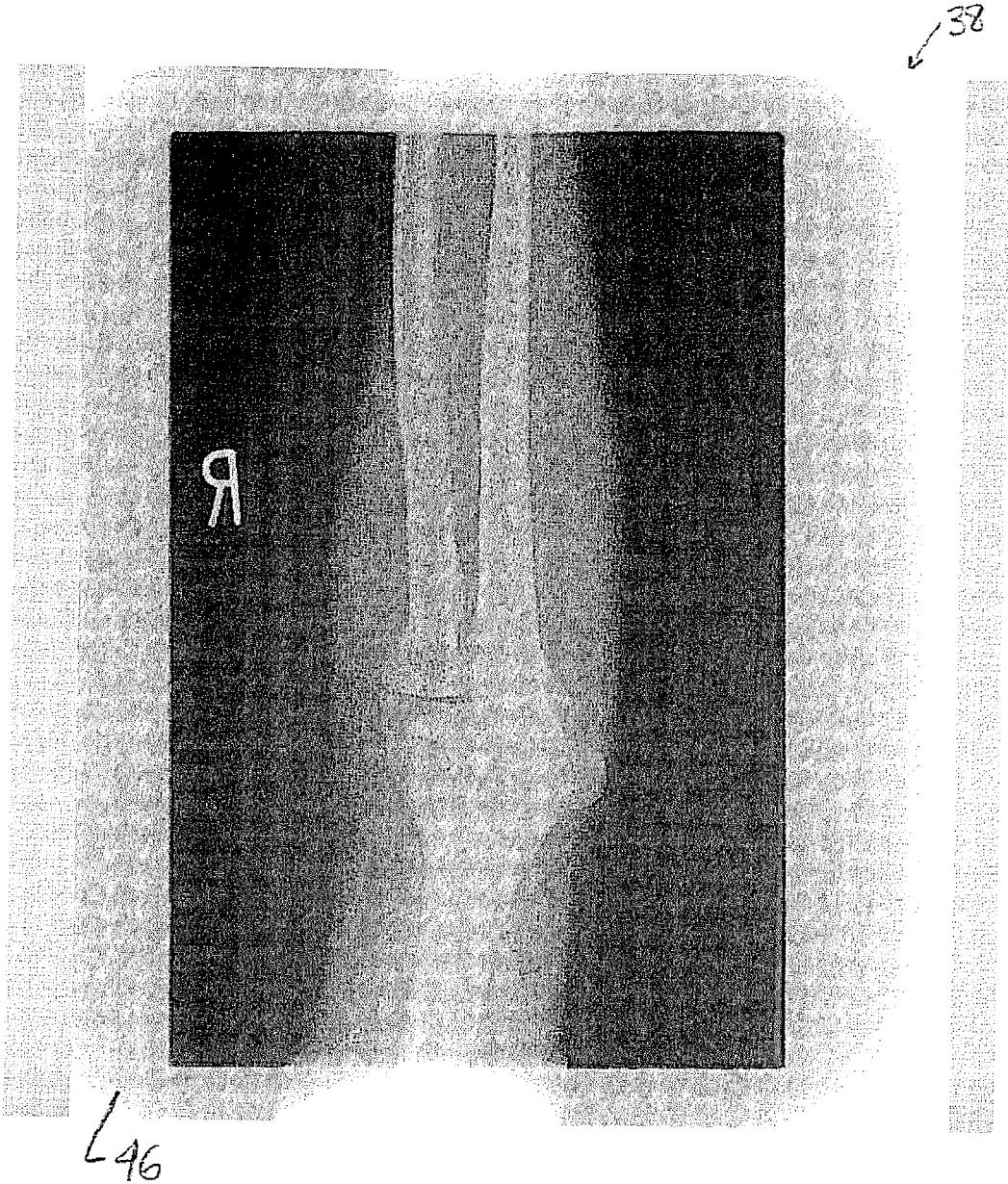
FIG. 3 is an x-ray image acquired using a shutter.

In step A, the image is acquired using, the X-ray apparatus 12. A technician positions the patient 22 between the photographic plate 20 and the shutter 16. The patient 22 can be positioned on a table, standing tip or in any other suitable arrangement. The shutter 16 is chosen to isolate a portion of the patient 22 according to the size of the aperture 18. It will be appreciated that the shutter 16 may be adjustable or interchangeable with other shutters having differently sized apertures and any other shuttered arrangement such as when using a lead apron. When commanded, the machine 26 powers the x-ray source 14 which then emits the x-ray beam 15 that passes through the isolated portion of the patient 22 and impinges on the photographic plate 20. The image processor 32 obtains the image data from the detection plate 20 and generates a 2-D array of intensities that represent the brightness in the image. The dark areas correspond to areas of soft tissue through which the x-rays pass, and the lighter areas correspond to denser tissues such as bone. An example of an x-ray image 38 of an elbow obtained using shutter 16 is shown in FIG. 3. As seen in FIG. 3, the image 38 includes a bright border 46 that corresponds to the shadow cast by the shutter 16 and includes the three bones that make up the elbow, namely the humerus, radius and ulna.

Figure 4:
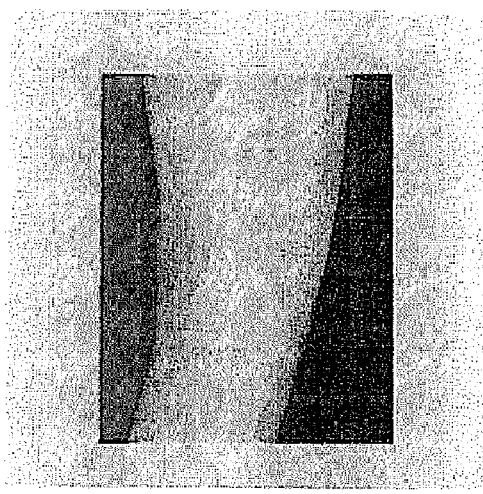
FIG. 4 shows a multiple resolution image pyramid for an x-ray image.
Figure 4:
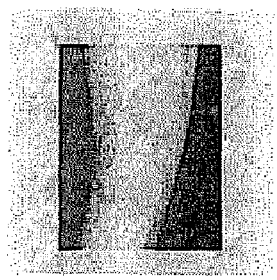
Figure 4:
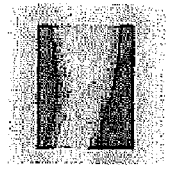
Figure 4:

In step B, the image processing program 26 preferably down samples the image generated in step A, since the original image is generally quite large, e.g. 2K-5K pixels×2K-5K pixels. The original image 38 can also be down-sampled by 4 to obtain an input image. The input image is then preferably further down sampled to reduce the size of the image and thus enable an increase in processing speed. It will be appreciated that any amount of down sampling can performed according to the speed requirements and the processing capabilities of the processing program 32. As such, depending on the processing capabilities of the system 10, a particular image size can be chosen and then a suitable number of stages between the input image and that particular size are generated. For example, as shown in FIG. 4, the input image (a) is first down sampled to the size of the nearest power of 2 that is smaller then the input image (a) to produce level 1 of the pyramid, namely image (b) (where the input image (a) is considered level 0 of the pyramid). Preferably, image (b) is further down sampled and then down sampled again until it reaches a desired size. For example, it has been found that a 128×128 pixel image provides adequate resolution with a decreased processing time when compared to the input image (a). In this example, in addition to level 0 and level 1, there are also levels 2 (image (c)) and 3 (image (d)), where image (d) is in this example the chosen fully downsampled size of 128×128 pixels. The images together create a multi-resolution pyramid representation of the input image (a) as shown in FIG. 4. The image pyramid is then used in steps C and D.

Figure 5:
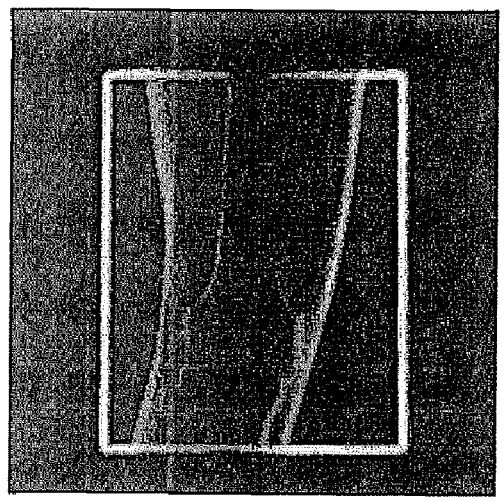
FIG. 5 is a series of gradient images for the image pyramid of FIG. 4.
Figure 5:
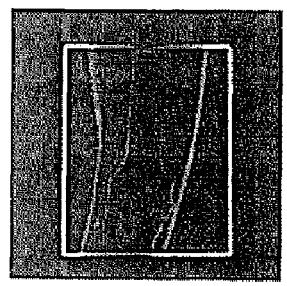
Figure 5:
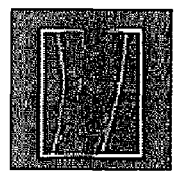
Figure 5:
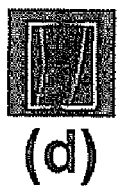
Figure 6:
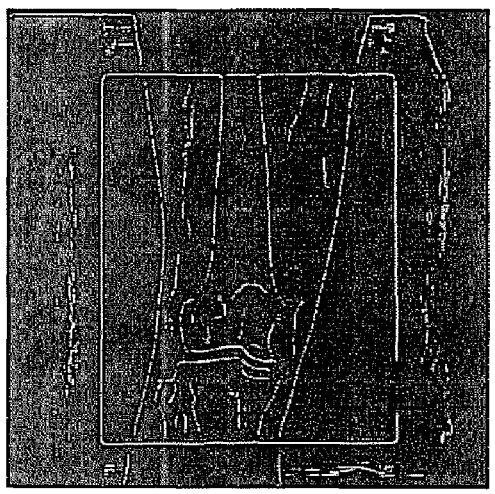
FIG. 6 is a series of edge mask images for the image pyramid of FIG. 4.
Figure 6:
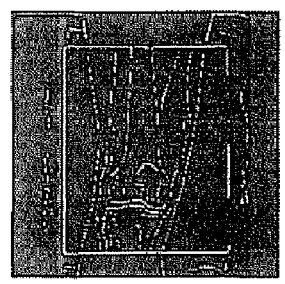
Figure 6:
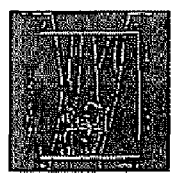
Figure 6:

In step C, the gradients for each image in the pyramid are calculated using a Sobel operator. A Sobel operator is a discrete differentiation operator commonly used in image processing applications, particularly in edge detection, that computes an approximation of the gradient of the image intensity at each point in the image. Typically, at each point, the result of the Sobel operator is either the corresponding gradient vector or the norm of this vector. This provides the direction of the largest possible increase from light to dark and the rate of chance in that direction. The result therefore shows how abruptly or smoothly the image changes at that point and how likely it is that the part of the image represents an edge. The Sobel operator is typically not directly applied to each image in the pyramid, but to its Gaussian blurred version. The purpose of Gaussian blur is for noise reduction. The lower the resolution of the image in the pyramid, the shorter the Gaussian kernel, in other words, the less blur it receives. The resultant gradient pyramid is shown in FIG. 5. It will be appreciated that any operator that creates an approximation of the gradient of the image intensity can be used and the Sobel operator is only one example.

In step D, the edge masks for each image in the pyramid are calculated using a Canny edge detector. The Canny algorithm is applied to the gradient pyramid result in Step C. It uses a number of masks to detect horizontal, vertical and diagonal edges and the results for each mask are stored. For each pixel, the largest result is marked at that pixel and the direction of the mask which produced that edge. The edges are then traced through the image using thresholding with hysteresis. The result is a binary image where each pixel is marked as either an edge pixel or a non-edge pixel. It will be understood that other edge masks can be used and the Canny algorithm is only one example.

The Canny algorithm includes adjustable parameters that can affect its effectiveness. For example, the use of two thresholds allows more flexibility than a single-threshold approach, but general problems of thresholding may still apply. A threshold that is set too high can miss important information and one that is set too low may falsely identify irrelevant information as being important. For x-ray images such as FIG. 3, it has been found that by setting the lower threshold to 0.5 and the upper threshold to 0.7, the results are generally sufficient for shutter detection.

Figure 9:
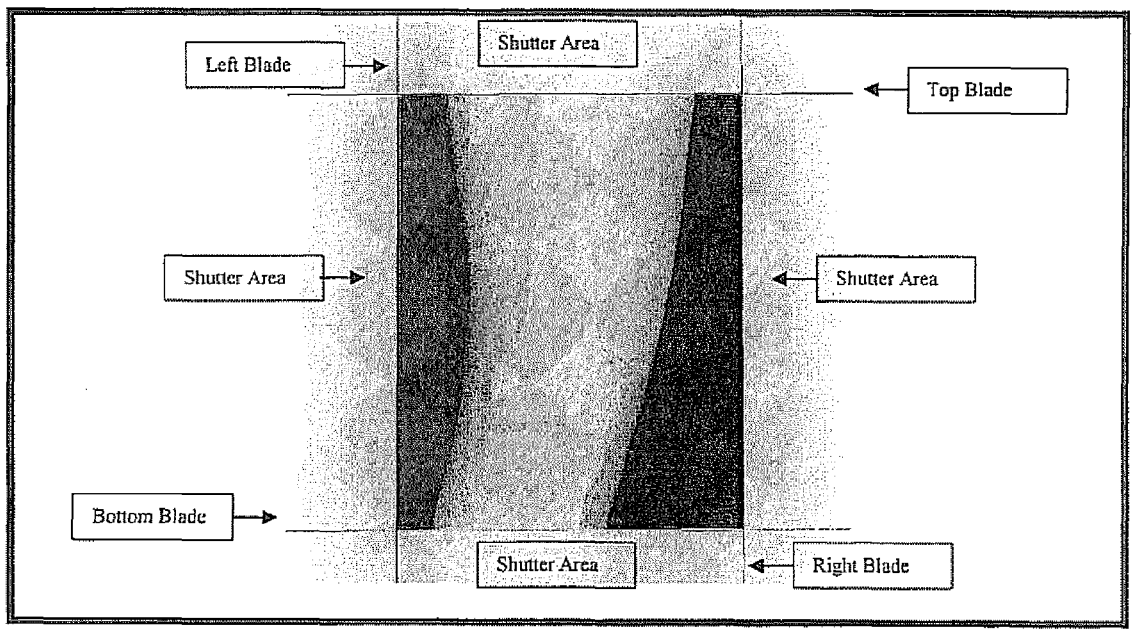
FIG. 9 shows another x-ray image acquired using a shutter and identifying shutter blades.

An objective of the shutter program 34 is to identify the shutter border 46 in the image 38 and automatically remove this data. The shutter border 46 is defined by the shutter 16 and, as explained above, may comprise any shape as dictated by the nature of the shutter 16. In this example, the aperture 18 is generally rectangular. The four shutter areas and the shutter blades defining the separation between the image data and the shutter data are best seen in FIG. 9. To ideally detect and remove the appropriate shutter areas, several assumptions should be made.

First, as discussed above, the shutter areas are generally brighter areas in the x-ray image. Second, the maximum number of shutter blades should be four in this example, assuming that the shutter has a conventional rectangular aperture 18. In other examples a different number of shutter blades may be expected such as three for a triangular aperture or one with a circular aperture. The four shutter blades shown in FIG. 9 are the top blade, the bottom blade, the left blade and the right blade. It should not be assumed that all expected blades will necessarily appear in every image since, due to changes in the procedure used, human error, etc., the aperture 18 may be misaligned or skewed with respect to the x-ray source 14 and, e.g. fewer than expected shutter areas are detected. The top and bottom blades will herein be referred together as the horizontal blade pair and the left and right blades will herein be referred together as the vertical blade pair.

Third, in this example, the shutter blades are assumed to be straight lines since the aperture 18 is typically rectangular. It will be appreciated that different assumptions would be required for differently shaped apertures such as curved or circular apertures (not shown). Fourth, if the blades of the horizontal blade pair are parallel then the two blades of the vertical blade pair are typically also parallel. However, if the shutter 16 is skewed with respect to the x-ray beam 15, the aperture can appear as a trapezoid in the image 38. In this case, either the vertical pair or horizontal pair will be parallel and the other pair will not. Similarly, the shutter blades should not be assumed to always be parallel to the image boundary since the shutter can be misaligned it due to human error or require a skewed orientation as dictated by the procedure being used. The shutter program 34 thus preferably accounts for these variations. Fifth, the horizontal blade pair is generally perpendicular to the vertical blade pair, however, the above-noted skewing of the shutter 16 can cause this to be untrue. Finally, the area of the image between the shutter blades and the image boundary are considered to be the shutter area.

Based on these considerations, two stages are performed to first detect a number of possible blade candidates, and then based on a heuristic rule set, identify the actual blade(s) and remove the shutter area 46. As noted above, the candidate blade detection stage 42 and the blade identification stage 44 are performed by the shutter program 34. It will be appreciated that the shutter program 34 is herein only conceptually independent of the image processing program 32 and may instead be embodied as a module or sub-routine within the program 32. In the blade detection stage 42, the shutter program 34 detects potential shutter blades in the image and the output is a sorted candidate list for each of the four blades. In the blade identification stage 44, the true shutter blades are identified from the candidate list.

In the blade detection stage 42, the potential blade candidates are first detected in the lowest resolution image in the image pyramid (e.g. image (d) or level 3 in FIG. 4). The candidates detected at each image level are promoted level by level up to the input image (a). At the next level, each candidate is re-evaluated and it is determined whether or not a better candidate in its vicinity exists. Those candidates that remain at the input image level (a) are promoted to the blade detection stage 44.

Figure 7:
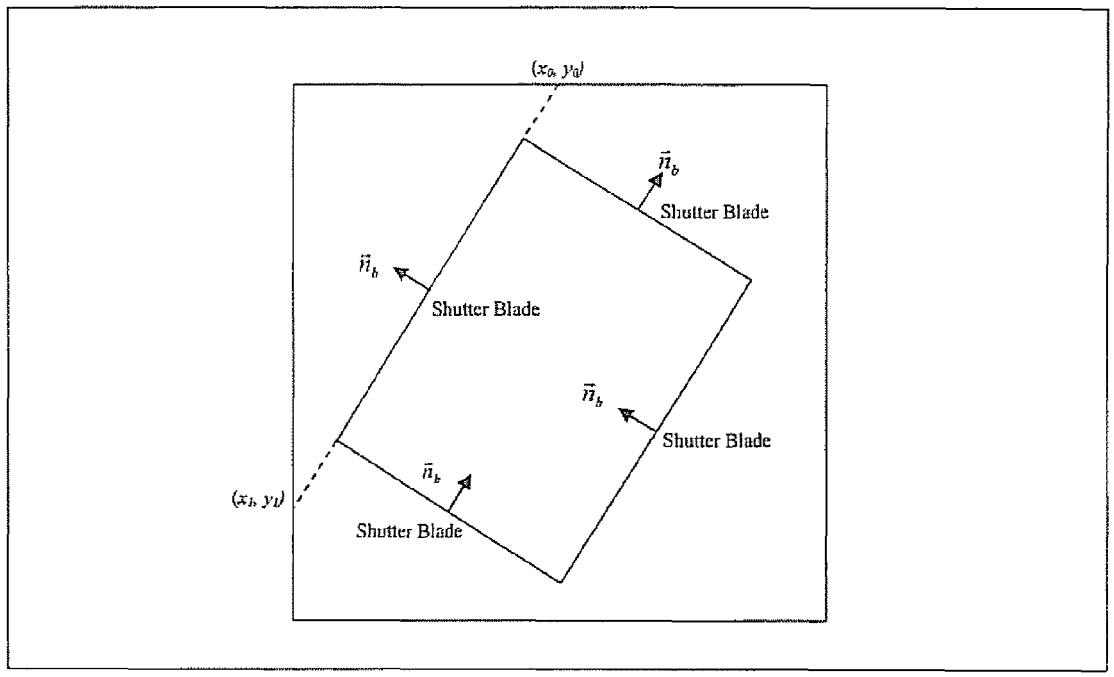
FIG. 7 is a diagram illustrating a shutter score definition.

A score function is used to evaluate the likelihood of the presence of a shutter blade. Each edge in the image can be evaluated as a potential shutter blade using the score function. An exemplary score function is shown in FIG. 7. The score function illustrated in FIG. 7 is based on prior knowledge of the nature of shutter blades, e.g., for a left shutter blade, the pixel values (brightness) in the shutter area (to the left of the blade) are generally greater than those of the adjacent image area (to the right of the blade). The score $S_b$ for a potential left shutter blade b which lies along a line defined by the points $(x_0, y_0)$ and $(x_1, y_1)$ can be calculated using the to following equation:

$$S_b = \sum_{i=0}^{m-1} (\vec{g}(x_i, y_i) \cdot \vec{n}_b) \cdot \text{Edge } (x_i, y_i)$$

The pair $(x_i, y_i)$ is a point on the shutter blade line b, $\vec{g}(x_i, y_i)$ is the gradient vector for point $(x_i, y_i)$ $\vec{n}_b$ is the normal vector for blade line b, m is equal to the image height for left and right blades (or the image width for top and bottom blades), and Edge$(x_i, y_i)$ is a binary value obtained from the corresponding edge mask at that image level. Typically, m represents the maximum number of pixels on the blade. For example, for left or right blades, the maximum number of possible pixels equals the image height. Based on this score function, a maximum value is given to a left or top blade and a minimum value is given to a right or bottom blade due to the orientation of the blade types in the image and the fact that the normal vector for left and right blades points in the left direction and the normal vector for top and bottom blades points in the top direction.

Preferably, an exhaustive evaluation is used for the detection of the potential shutter blades, whereby the scores for all possible horizontal and vertical blades that intersect with the image are calculated. The result of the exhaustive evaluation is a score map which shows the likelihood of the presence of a shutter blade.

Figure 8:
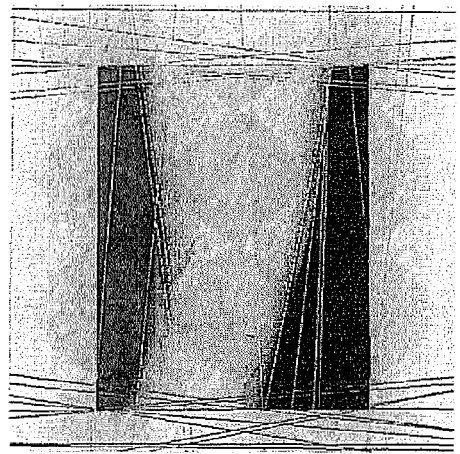
FIG. 8 shows the image of FIG. 3 with blade candidates.

From the score map, a selection of the top candidates is then chosen for each of the blades. Any number of candidates can be chosen depending on the application and preferably, the program 34 should be able to accommodate the use of different parameters. It has been found that choosing the top 16 candidates provides an adequate number of candidates to avoid missing the true shutter blades. The top candidates are first chosen in level (d) and then successively promoted to the next image level in the pyramid up to the input image level (a) as seen in FIG. 8. The promotion of the blade candidates at each level is used to optimize the blade score.

First, each candidate is scaled up to the next resolution level and an exhaustive search is performed in the candidate's spatial neighborhood to determine if there is a better approximation. Any size of spatial neighborhood can be chosen depending on the resolution of the image etc. It has been found that a radius of 2 pixels from the ends of the blades is sufficient in this example.

Second, once the candidates are selected, they are compared to each other. If two candidates being compared are sufficiently "close" spatially, the one with the higher score is kept and the other discarded. The degree of spatial "closeness" can vary based on the application. For example, if both the distance between the start and end points of the two blade candidates is within tan(3°)*max(image width, image height), the blades have been found to be considered "close". In this example, the resulting 16 best candidates for each blade are detected at the input level (a) as shown in FIG. 8.

The top candidates detected at the input image level (a) are promoted to the blade identification stage 44. As noted above, the blade identification stage 44 is used to distinguish the true shutter 22 blades from false positive candidate blades. False positives are generally detected due to the presence of human anatomy such as an aim, rib cage etc. The identification stage 44 uses a heuristic rule set for validating each blade candidate based on a set of properties for each candidate.

The blade properties are calculated using the input image 4(*a*) and its corresponding gradient 5(*a*) and edge mask 6(*a*). There are a number of blade properties that can be considered. The following discusses those properties that have been found to be useful in candidate blade identification 44.

Typically, each blade candidate can be segmented. If part of the blade candidate is coincident with a continuous edge in the edge mask, it can be considered a blade segment. Such segments generally have a high probability of being part of a shutter blade and thus the properties for the blade are measured in the segments only. Each blade candidate may have several segments. The segment length may be defined as the number of connected pixels in the edge mask that are coincident with the particular blade candidate being considered. Each blade segment has a blade segment external mean, which is the mean pixel value of a windowed area on the shutter area side of the blade segment. As the shutter is typically towards the edge of the image, the shutter area side is typically on the side of the blade that is further away from the centre of the image. Each blade segment has a blade segment internal mean, which is the mean pixel value of a window area on the image area side of the blade segment. The image is typically within the shutter 16 and thus the image area side is typically the side of the blade which is closer to the centre of the image. The window can be any suitable size depending on the size of the image and the allocated processing time to such an operation. It has been found for this example that a window size of 40× the length of the segment (in pixels) is suitable.

The blade segment gradient angle mean can also be considered, which is the mean of the gradient angle for the pixels on the blade segment, as well as the blade segment gradient standard deviation, which is the standard deviation of the gradient angle for the pixels on the blade segment.

At the blade level, the blade external mean can be considered, which is the mean of the external mean values for the blade segments for that particular blade. Similarly, the blade internal mean can be considered, which is the mean of the internal mean values for the blade segments for that particular blade.

For the shutters, the shutter area for each blade candidate can be considered, which is the number of pixels in the shutter area defined by that particular blade candidate. The shutter area mean (average pixel value in shutter area) and shutter area standard deviation (standard deviation of the pixel values in the shutter area) can also be considered. It has also been found that the number of direct exposure pixels in the shutter area can be a useful property to consider.

The following example heuristic rule set is applied to the blade candidates taking the above properties into consideration, preferably, in the order in which they are described. It will be appreciated that any or all of the heuristic rules described below can instead be implemented using a classifier.

Classifiers are a class of algorithms which can 'learn' heuristic rules through observing various examples. The most commonly used classifiers are the Neural Network, decision tree and linear classifiers.

In order to use a classifier, the features, including the ones described above, are represented by a feature vector. In the first phase the classifier is 'trained' on a set of images in which the human operator has manually defined the shutter blades. In this phase the classifier would be provided with a set of 'positive' examples, (e.g. feature vectors which represent true blades) and a set of 'negative' examples, (e.g. features vectors which do not represent blades, but rather anatomy or hardware in the image). Based on these examples the classifier partitions the feature space into two regions: 1) Where vectors represent blades, and 2) Where vectors are not blades. The specifics of the training phase typically depend on the type classifier selected.

In a second phase, the classifier is deployed in the actual application, where it is actually presented to a feature vector and asked to determined whether it is a true blade or a false positive such as anatomy in the image. Based on the partition computed in the 'training' phase the classifier will provide the classification result. It may be noted that the first phase, namely the 'training' phase, is typically done only during a software development stage. Once the software is deployed in the imaging system, the software only performs the classification based on the outcome of the training phase. As such, additional training may be beneficial if the classification is not performing, as intended or if other false positives are discovered.

Figure 11:
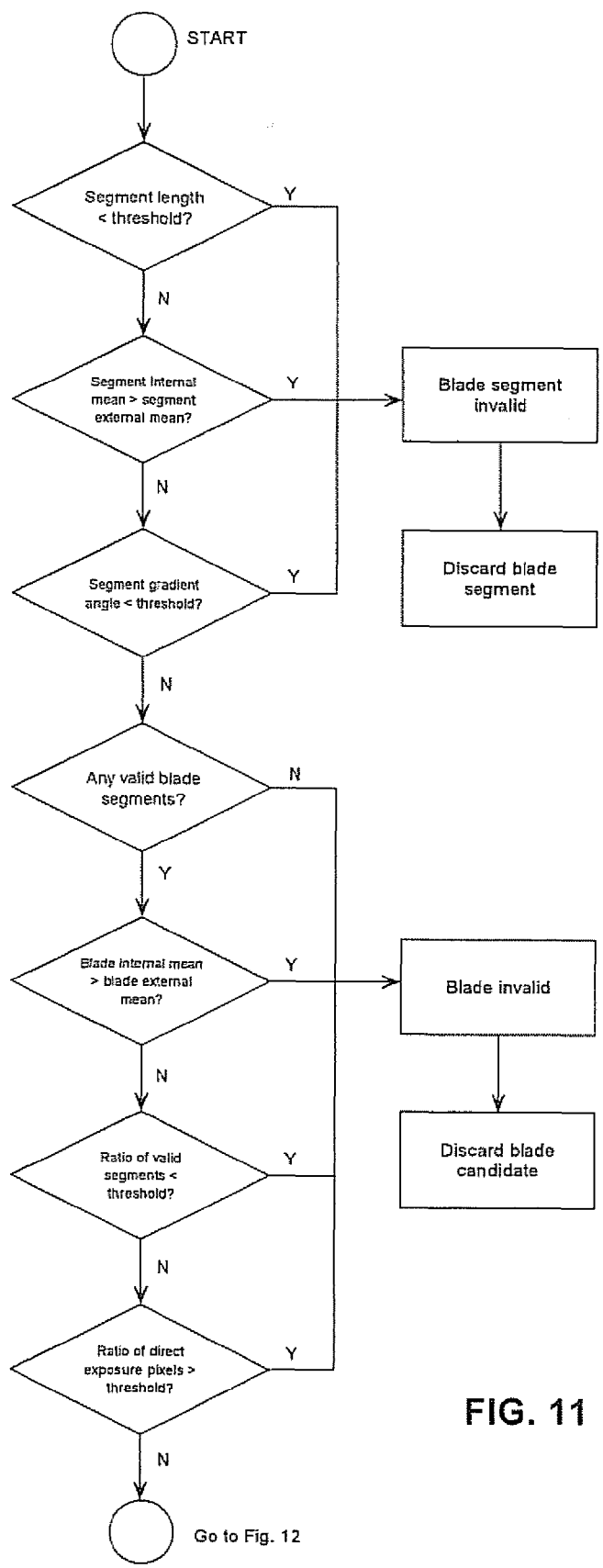
FIG. 11 is a flowchart illustrating an application of a heuristic rule set.
Figure 12:
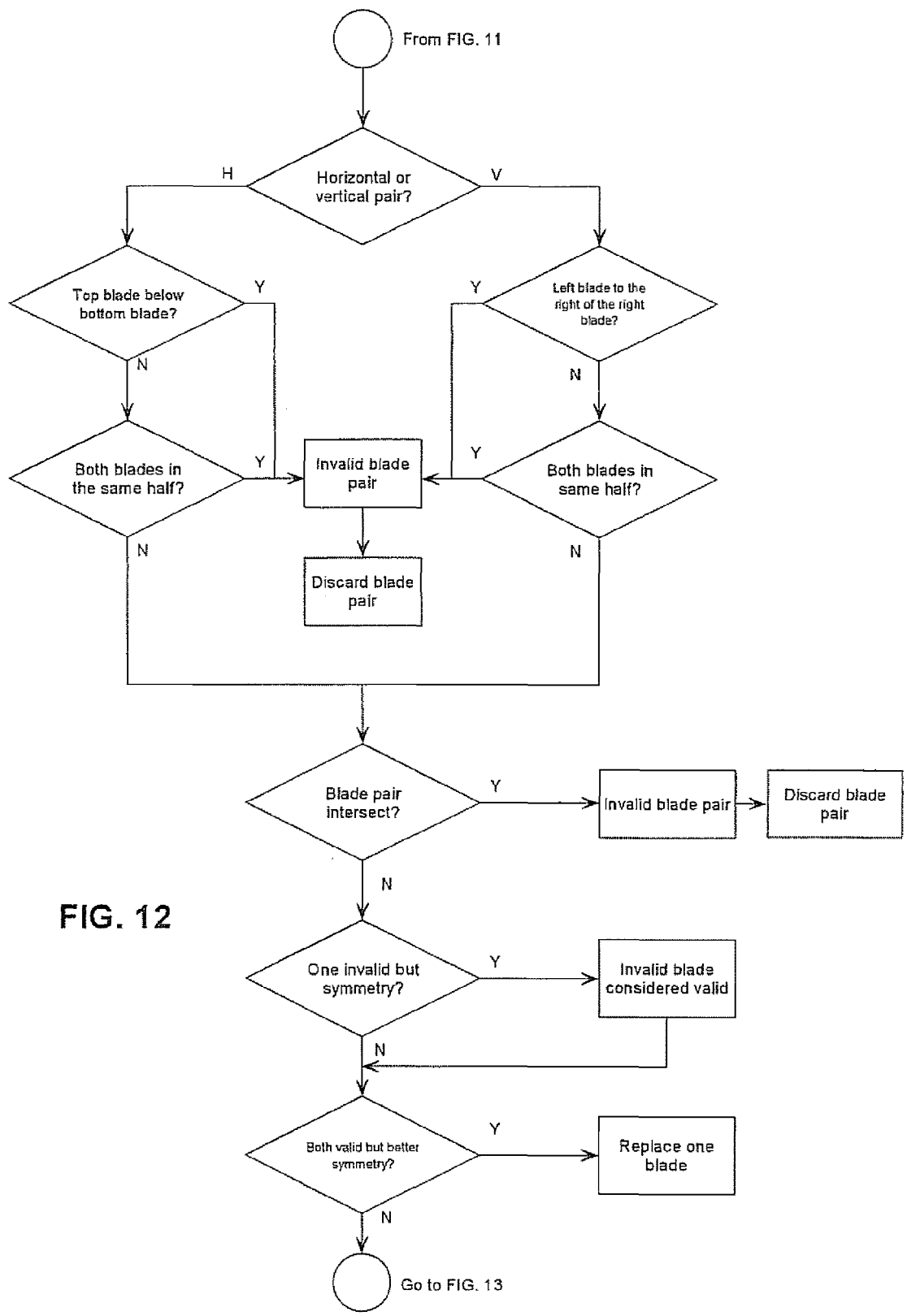
FIG. 12 is a flowchart continuing from FIG. 11.
Figure 13:
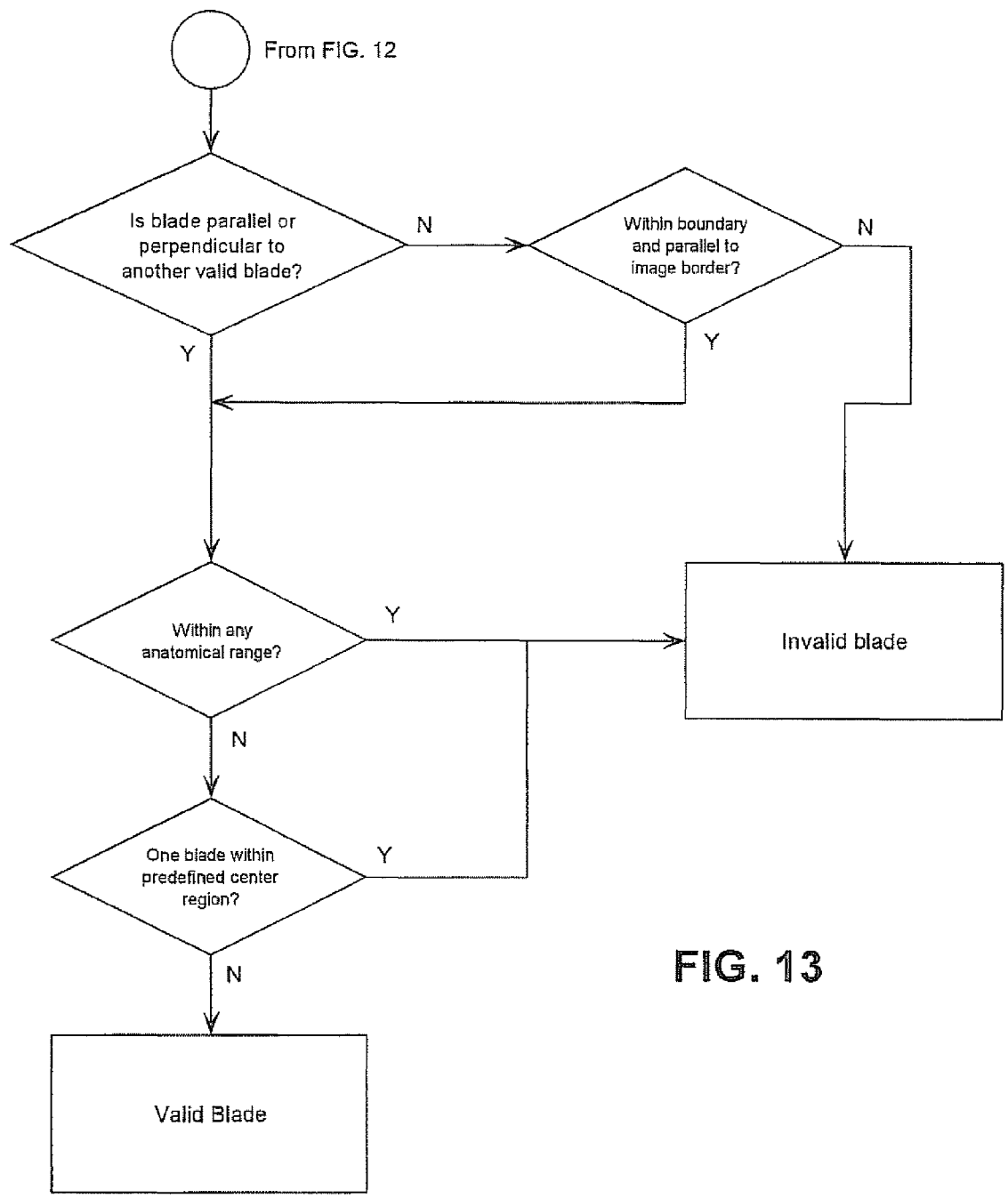
FIG. 13 is a flowchart continuing from FIG. 12.

The application of the rule set is shown in FIGS. 11-13. First, a blade segment verification is performed for each segment in the candidate blade at the segment level. If a blade's blade segment length property is smaller than a predefined threshold, the segment is considered to be invalid, since where the blade segment is too small, it typically does not contribute to the blade internal mean and blade external mean properties. It has been found that the threshold is dependent on the application and thus should preferably be changeable. Also, if the blade segment's blade internal mean is greater than its blade external mean value, the segment is considered to be invalid. For example, for a blade that is considered to be a left blade, the external mean is calculated to the left of the blade and the internal mean to the right of the blade. A higher internal mean indicates that the blade is likely an anatomical stricture where the pixels are in fact brighter to the right of the blade and darker to the left, i.e. the transition from right to left is bright-to-dark whereas a true blade would transition dark-to-bright (see FIG. 9). Similarly, if a blade segment's gradient angle similar direction ratio property is below a predefined threshold such as 0.5, the segment is considered invalid, since for trite blades, the gradient along the blade should have a substantially similar direction, whereas for a false blade, e.g. caused by anatomy, the gradient direction along the blade is typically quite different.

As noted above, this step could be replaced by a classifier. In such a case, the value of the blade length, internal and external means, gradient strength, etc., will be included in the set of features provided to the classifier in the training and deployment phases, in the same way such inputs would be fed into the heuristic rules.

Second, a single blade identification is performed for each blade candidate at the blade level. If a single blade does not contain any valid segments then the blade candidate is considered invalid. If a blade's internal mean property is greater that its blade external mean property then the blade is considered invalid since this would indicate an improper transition from dark- to bright and vice versa. If the ratio of the number of valid segments to the number of total blade segments for a particular blade candidate is below a predetermined threshold such as 0.35, the blade is considered invalid since, for a true blade, a majority of its segments should be valid segments. Finally, if the ratio of the number of direct exposure pixels in the shutter area to the total shutter area defined by the candidate blade is above a predetermined application-dependent threshold, the blade is considered invalid, since for a true blade, ideally there should be no direct exposure pixels in its blade area.

Again, this step can be replaced with a classifier, where the number of valid segments, internal an external means, area and ratio of valid segments, etc., will be included in the set of features provided to the classifier during the training and deployment phases. It can be seen that the heuristics described herein can be accomplished through application of the individual steps as discussed, or automated using classifiers. This is applicable to the remaining rules.

Next, a set of rules based on blade pairings is considered as shown in FIG. 12. Each candidate blade is compared with others of similar orientation, in this example, horizontal or vertically aligned. For example, a blade may be considered horizontal if it is within ±45° of the true horizontal in the image to accommodate for a skewed shutter etc. First, it is determined whether the blade pair is horizontally aligned or vertically aligned. When the blade pair is horizontal, it is first determined whether or not what is considered the top blade is actually above what is considered the bottom blade. As noted above, each blade, when identified as a blade candidate, is classified as top, bottom, left or right based on the transitions from dark to bright and vice versa.

If the "top" blade is not above the "bottom" blade then the pair is considered invalid and both blade candidates are discarded. Also, if both blades are found in the same half of the image e.g. both are found in the top half of the image, then the blade pair is found to be invalid.

When the blade pair is vertical (left and right pair), it is first determined whether or not what is considered the left blade is actually positioned to the left of what is considered the right blade. It is also determined whether or not the blades are in the same half and whether or not the distance between the blades is below the predetermined threshold. Those pairs that are not considered invalid are then further evaluated.

If the blade pairs intersect, either within the image or within a certain range outside of the image, such as one image width or height, the blade pair is considered invalid. Due to human error and/or depending on the x-ray procedure, the shutter can be skewed with respect to the plate 20, which results in a slight perspective view of the aperture 18 in the image. In this case, the true blades would intersect at some point beyond the image, however, the range outside of the image is chosen to tolerate such error. If the blade pair converges very rapidly (or diverges rapidly) then it is likely that the blades do not constitute a pair and at least one of them is likely not a true shutter blade.

Where one blade in the pair is considered invalid but the other is considered valid, a symmetry rule can then be applied. If only one blade in the pair is valid but the other invalid blade possesses symmetry with the valid blade about the center of the image and substantially parallel to the valid blade, the invalid blade is re-classified as "valid" and the next rule is applied. Typically, there is an application tolerance for determining how parallel a blade is, e.g. a tolerance of between 5 to 7 degrees is suitable. In the next rule, where both blades in the pair are valid but there is/are other blade candidate(s) which possess more symmetry than the particular pair, then the more symmetric pair will replace this pair as the valid left/right or top/bottom-blade pair. This operation is performed to find the best match for each blade candidate.

As seen in FIG. 13, all the valid blades that remain are then subjected to a configuration identification rule. The relative position of all valid blades is checked. If a blade is not substantially parallel or substantially perpendicular to any other valid blades, it is deemed to be invalid, unless it falls within a predefined range near the boundary of the image, which is typically application dependent, and is parallel to the boundary of the image. In the present example, a border between 0.15 and 0.25 of the image area has been found suitable. This second check will accommodate those blades that are near enough to the boundary to likely be a true blade but do not align as expected with the other blades. For example, skewing in the image can cause slight convergence or divergence between blades, however, the blade can still be parallel to the boundary and close enough to it that it may be a true shutter blade.

A number of rules related to anatomical identification are then performed. In x-ray images, edges from the arm and rib cage have similar properties to shutter blades and thus may generate a false positive, even when subjected to the above rules. However, true shutter blades, if present, often appear near the border of the image. Therefore, valid blade candidates within a central range of the image are considered to be invalid as they are likely caused by an anatomical structure. Similar false positives can be generated by the presence of shoulder anterior/posterior or posterior/anterior strictures in the image, as well as pelvis and hip structures. Again, these structure should appear within the central portion of the image in relation to those that are true shutter blades.

A final configuration identification is performed where only one valid blade candidate remains. If this blade appears in the predefined central region of the image, then it is considered invalid.

Figure 10:
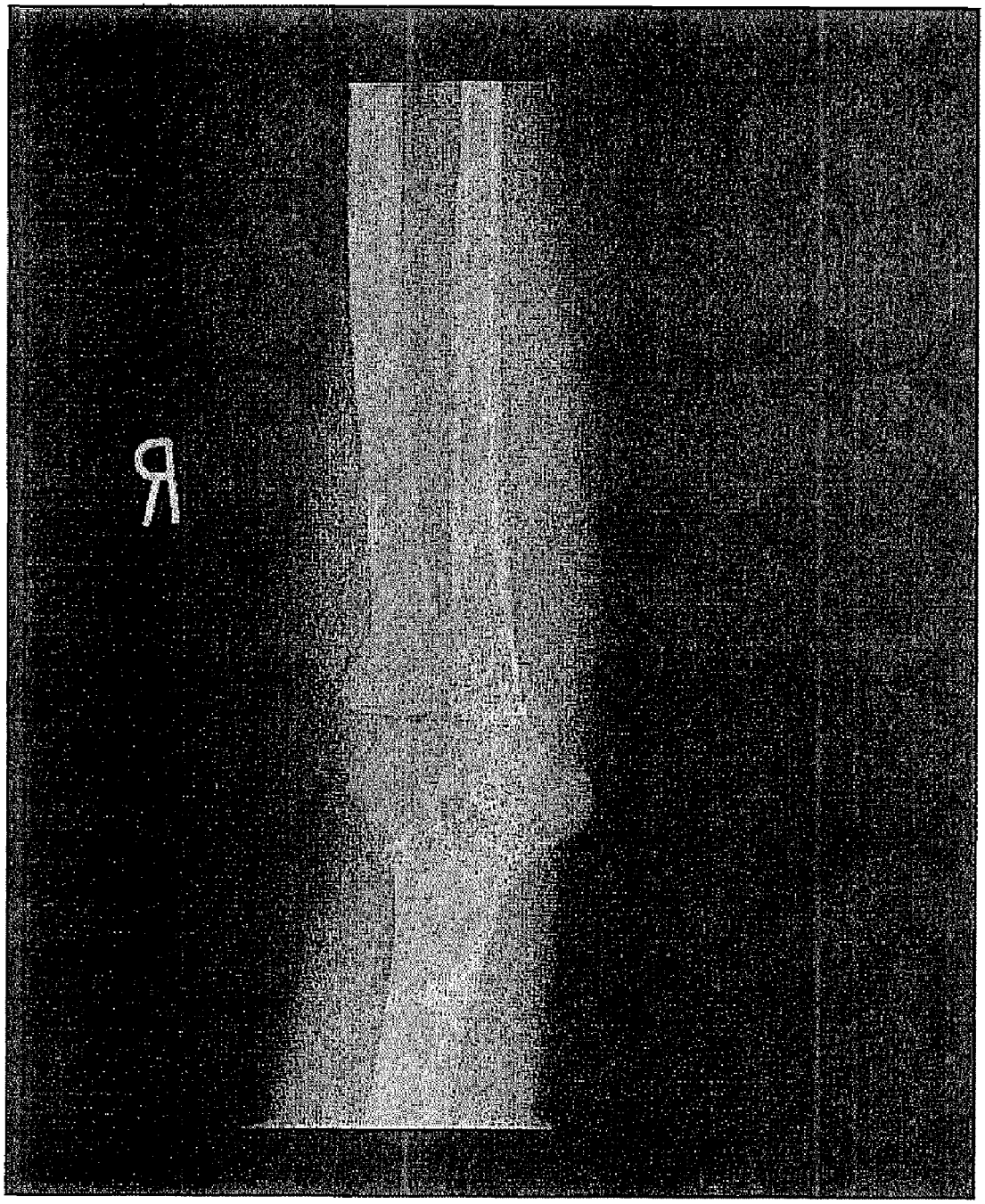
FIG. 10 shows the image of FIG. 3 with the shutter portions removed.

Upon applying the heuristic rule set to each of the candidate blade, using the remaining valid blades, the shutter is determined and the unwanted portion(s) of the image is/are removed to provide the processed image shown in FIG. 10 as an output to the display 28.

It is therefore seen that the use of an exhaustive identification of blade candidates and the application of a heuristic rule set allows the automatic detection and removal of shutter areas in an x-ray image. Naturally, the above principles are also applicable to other imaging systems that include bright, diagnostically useless areas wherein it would be beneficial to remove such areas. It will be appreciated that any combination of rules or variations of those above can be used as deemed suitable for the particular operation. For example, the tolerances can be adjusted based on inaccuracies from the x-ray apparatus 12 or based on the types of anatomical structures that are being imaged and/or shutter types being used. For elongated bone structures, it may only be necessary to look at whether or not vertical blade pairs lie within the central region of the image since it would be unlikely that horizontal false positives are detected. It will be understood that all tolerances and parameters exemplified above are for illustrative purposes only. Preferably, any such tolerances and parameters are capable of being modified to suit a particular application and/or vendor such that the system 26 is applicable to any medical imaging application.

Although the invention has been described with reference to certain specific embodiments, various modifications thereof will be apparent to those skilled in the art without departing from the spirit and scope of the invention as outlined in the claims appended hereto.

The invention claimed is:

1. A method for detecting and removing unwanted information in a medical image comprising:
processing said image to obtain edge information, wherein said processing comprises down sampling said image to generate a plurality of image levels having successively decreasing image resolutions;
generating a list of at least one candidate edge in said image from said edge information according to predetermined criteria, wherein each of said at least one candidate edge corresponds to a single blade of a shutter used to generate said image, the shutter including a plurality of blades, and wherein said list is generated by selecting a first candidate list at a lowest of said plurality of image levels, and promoting said first candidate list through subsequent image levels until a highest of said image levels and using candidate edges promoted to said highest of said image levels as said list of at least one candidate edge;
evaluating each of said at least one candidate edge according to a predetermined rule set to select one or more of said at least one candidate edge that is considered to define the extent of said unwanted information within said image, said evaluating comprising comparing said at least one candidate edge to other information in said image; and
removing said unwanted information based on the location of said one or more of said at least one candidate edge in said image.

2. The method according to claim 1 wherein said at least one candidate edge is chosen by applying a score function to edges detected in said image.

3. The method according to claim 1 wherein said evaluating each of said at least one candidate edge comprises evaluating properties of one or more segments for each said at least one candidate edge.

4. The method according to claim 1 wherein said evaluating each of said at least one candidate edge comprises evaluating properties of candidate edges according to the orientation of said candidate edges in said image, said properties being those associated with an image side of said candidate edges closer to a center of said image and a shutter side of said candidate edges further away from said center of said image.

5. The method according to claim 1 wherein said predetermined rule set is prepared using one or more classifiers applied during a training phase.

6. The method according to claim 1 wherein said evaluating each of said at least one candidate edge comprises evaluating pairs of candidate edges having similar orientations.

7. The method according to claim 1 wherein said evaluating each of said at least one candidate edge comprises considering predetermined properties of anatomy to discard false positives.

8. A computer readable medium carrying computer executable instructions for causing an image processing device to execute the method according to claim 1.

9. A system for detecting and removing unwanted information in a medical image comprising:
an interface comprising a display for viewing said image and enabling a user to interact with said system; and
an image processing program capable of obtaining and processing said image from a medical imaging device and displaying said image on said display, said image processing program being configured for
processing said image to obtain edge information, wherein said processing comprises down sampling said image to generate a plurality of image levels having successively decreasing image resolutions;
generating a list of at least one candidate edge in said image from said edge information according to predetermined criteria, wherein each of said at least one candidate edge corresponds to a single blade of a shutter used to generate said image, the shutter including a plurality of blades and wherein said list is generated by selecting a first candidate list at a lowest of said plurality of image levels, and promoting said first candidate list through subsequent image levels until a highest of said image levels and using candidate edges promoted to said highest of said image levels as said list of at least one candidate edge;
evaluating each of said at least one candidate edge according to a predetermined rule set to select one or more of said at least one candidate edge that is considered to define the extent of said unwanted information within said image, said evaluating comprising comparing said at least one candidate edge to other information in said image; and
removing said unwanted information based on the location of said one or more of said at least one candidate edge in said image.

10. The system according to claim 9 wherein said at least one candidate edge is chosen by applying a score function to edges detected in said image.

11. The system according to claim 9 wherein said evaluating each of said at least one candidate edge comprises evaluating properties of one or more segments for each said at least one candidate edge.

12. The system according to claim 9 wherein said evaluating each of said at least one candidate edge comprises evaluating properties of candidate edges according to the orientation of said candidate edges in said image, said properties being those associated with an image side of said candidate edges closer to a center of said image and a shutter side of said candidate edges further away from said center of said image.

13. The system according to claim 9 wherein said predetermined rule set is prepared using one or more classifiers applied during a training phase.

14. The system according to claim 9 wherein said evaluating each of said at least one candidate edge comprises evaluating pairs of candidate edges having similar orientations.

15. The method according to claim 1 wherein said evaluating each of said at least one candidate edge comprises considering predetermined properties of anatomy to discard false positives.

* * * * *

UNITED STATES PATENT AND TRADEMARK OFFICE
CERTIFICATE OF CORRECTION

PATENT NO.        : 8,218,879 B2
APPLICATION NO.   : 11/857546
DATED             : July 10, 2012
INVENTOR(S)       : Songyang Yu, Vittorio Accomazzi and Paul Geiger Page 1 of 1

It is certified that error appears in the above-identified patent and that said Letters Patent is hereby corrected as shown below:

In the Specification

Column 1, line 18: "are typically used to shield body pails" should be --are typically used to shield body parts--.

Signed and Sealed this
Twenty-fifth Day of February, 2014

Michelle K. Lee
*Deputy Director of the United States Patent and Trademark Office*